(12) United States Patent
Yue

(10) Patent No.: US 7,135,036 B2
(45) Date of Patent: Nov. 14, 2006

(54) HEATING PAD HAVING A PHASE CHANGE MATERIAL

(76) Inventor: Steven Yue, 4F, No. 7, Lane 180, Sec. 2, Yen-Chiu-Yuan Rd., Nan-Kang Dist., Taipei (TW)

( * ) Notice: Subject to any disclaimer, the term of this patent is extended or adjusted under 35 U.S.C. 154(b) by 183 days.

(21) Appl. No.: 10/849,723

(22) Filed: May 20, 2004

(65) Prior Publication Data

US 2005/0021115 A1    Jan. 27, 2005

(30) Foreign Application Priority Data

Jun. 27, 2003    (CN)    .............................. 03 2 66285

(51) Int. Cl.
*A61F 7/00*    (2006.01)
*A61F 7/12*    (2006.01)

(52) U.S. Cl. .................... 607/96; 607/108; 606/27; 219/528

(58) Field of Classification Search ............. 219/212, 219/217, 387, 528; 606/27; 607/96, 98, 607/99, 108–111
See application file for complete search history.

(56) References Cited

U.S. PATENT DOCUMENTS

| | | | | | |
|---|---|---|---|---|---|
| 5,150,707 | A | * | 9/1992 | Anderson | 607/114 |
| 5,892,202 | A | * | 4/1999 | Baldwin et al. | 219/387 |
| 6,329,644 | B1 | * | 12/2001 | Hyatt | 219/528 |
| 2002/0092838 | A1 | * | 7/2002 | Bostic et al. | 219/387 |

* cited by examiner

*Primary Examiner*—Linda C. M. Dvorak
*Assistant Examiner*—Alex Toy
(74) *Attorney, Agent, or Firm*—Ohlandt, Greeley, Ruggiero & Perle, L.L.P.

(57) ABSTRACT

A heating pad includes an envelope containing a heating unit and a phase change material which encloses the heating unit. The heating unit includes a metal plate and a resistance heating element attached to the metal plate. Flexible strips are disposed within the envelope by attachment to the envelope, and the metal plate is positioned within the envelope through the strips. A pair of electrodes are connected to the heating element and extend outwardly of the envelope. The phase change material can undergo a phase change process through the heating unit so that no external heat source is needed to heat the phase change material.

9 Claims, 4 Drawing Sheets

US 7,135,036 B2

HEATING PAD HAVING A PHASE CHANGE MATERIAL

CROSS-REFERENCE TO RELATED APPLICATION

This application claims priority of Chinese Patent Application No. 03266285.8 filed on Jun. 27, 2003.

BACKGROUND OF THE INVENTION

1. Field of the Invention

This invention relates to a heating pad, more particularly to a heating pad having a phase change material.

2. Description of the Related Art

A therapeutic heating pad which is made of a phase change or thermal energy storage material typically includes an envelope 1 filled with a phase change material 10, as shown in FIG. 1. The phase change material is in a solid or gel-like format normal or room temperature. When the heating pad is to be used, it is put into water and heated so that the phase change material absorbs heat and is transformed into liquid, thus storing thermal energy. At this time, the heating pad can supply heat for therapeutic purposes. When the phase change material becomes cold due to its liberation of heat, the phase change material returns to its solid or gel state. While such a heating pad has a simple construction, because the heating pad must be heated in water, it is suitable only for the household use. The application thereof is therefore limited.

FIG. 2 shows another conventional heating pad 1A which contains a liquid state phase change material 11 enclosing a metal plate 12. When it is used, a force is applied to the metal plate 12 to deform the metal plate 12. The phase change material 11 which is in the liquid state begins to liberate heat and change into a gel-like form. This heating pad 1A is also simple in construction. However, when the heating pad 1A is to be reused, it must be heated in water to cause the phase change material 11 to return to its liquid form from the gel-like form. Therefore, the application of the heating pad 1A is also limited. It is thus desirable to develop a heating pad with a self-heating means to heat a phase change material contained therein.

SUMMARY OF THE INVENTION

An object of the present invention is to provide a heating pad with a self-heating unit so that a phase change material contained therein can be heated without using water and external heat source.

According to the present invention, a heating pad comprises: an envelope confining a receiving space; a heating unit including a metal plate, and a resistance heating element attached to the metal plate; a positioning unit mounted within the receiving space and connected to the metal plate; a phase change material provided within the receiving space and enclosing the heating unit; and a pair of electrodes connected to the heating element and extending outwardly of the envelope.

BRIEF DESCRIPTION OF THE DRAWINGS

Other features and advantages of the present invention will become apparent in the following detailed description of the preferred embodiments of the invention, with reference to the accompanying drawings, in which.

DETAILED DESCRIPTION OF THE PREFERRED EMBODIMENTS

Figure 1:
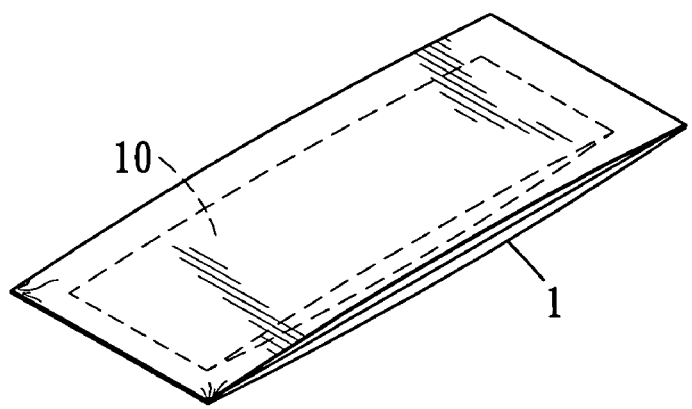
FIG. 1 is a schematic view of a conventional heating pad.
Figure 2:
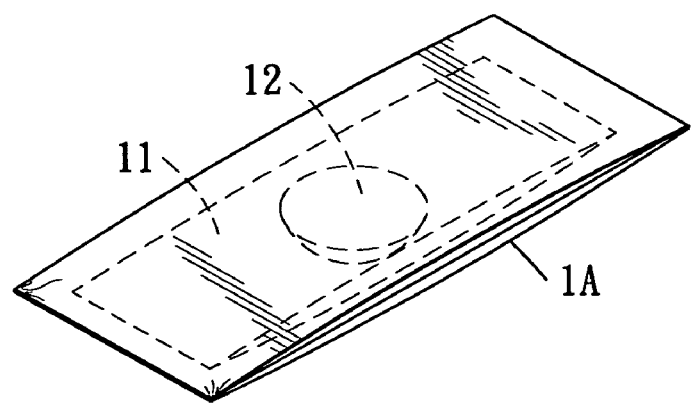
FIG. 2 is a schematic view of another conventional heating pad.

Before the present invention is described in greater detail, it should be noted that same reference numerals have been used to denote like elements throughout the specification.

Figure 3:
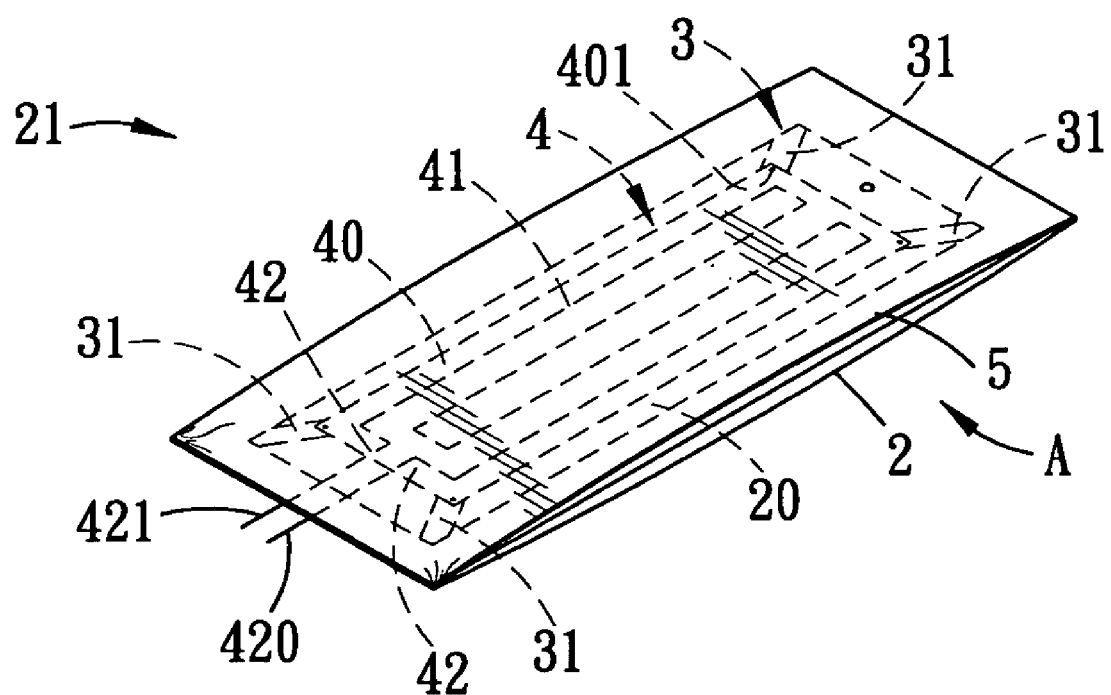
FIG. 3 is a perspective view of a heating pad embodying the present invention.

Referring to FIG. 3, a heating pad embodying the present invention is shown as being a therapeutic heating pad (A) which includes an envelope 2 that confines a receiving space 20. The envelope 2 is made of a material which is leakproof and which is durable and strong enough to prevent breakage. In this embodiment, the envelope 2 is made of a plastic material such as polyethylene or an aluminum foil. A positioning unit 3 is disposed within the receiving space 20 to position a heating unit 4 inside the receiving space 20.

The heating unit 4 includes a metal plate 40 and a resistance heating element 41 attached to the metal plate 40. The resistance heating element 41 is insulated, and may be a resistance coil bonded to the metal plate 40, or a resistance wire printed on the metal plate 40. The positioning unit 3 includes four flexible strips 31 attached respectively to four corners of the envelope 2 by, for example, a thermal bonding process, so that they are hung on the four corners of the envelope 2. The other ends of the strips 31 are connected respectively to four corners of the metal plate 40. The strips 31 in this embodiment are made of the same material as the envelope 2, and each strip 31 is attached to the metal plate 40 by extending through one of the holes 401 formed in the metal plate 40.

The heating pad (A) further includes a thermal storage material, such as a phase change material 5, which is received by the receiving space 20 of the envelope 2. The phase change material 5 encloses entirely the heating unit 4.

A pair of electrodes 42 are connected respectively to two ends of the resistance heating element 41 and have ends 420, 421 which extend out of the envelope 2. The ends 420, 421 may be connected to a power source, such as a battery assembly (not shown).

When the ends 420 and 421 of the electrodes 42 are connected electrically to a power source, the resistance heating element 41 of the heating unit 4 will generate heat which will be transferred to the metal plate 40, thereby heating the phase change material 5. When the temperature of the heating pad (A) reaches a desired level, the heating element 41 can be disconnected from the power source. As the phase change material 5 is heated, it undergoes a phase change process and stores thermal energy which can be supplied to a patient for therapy. When the heating pad (A) or the phase change material 5 becomes cold, the heating unit 4 may be connected to the power source once again to heat the phase change material 5. As the heating pad (A) of the present invention is provided with the heating unit 4 which can be connected to a battery assembly to heat the phase change material 5, the heating pad (A) may be conveniently used either indoors or outdoors.

Figure 4:
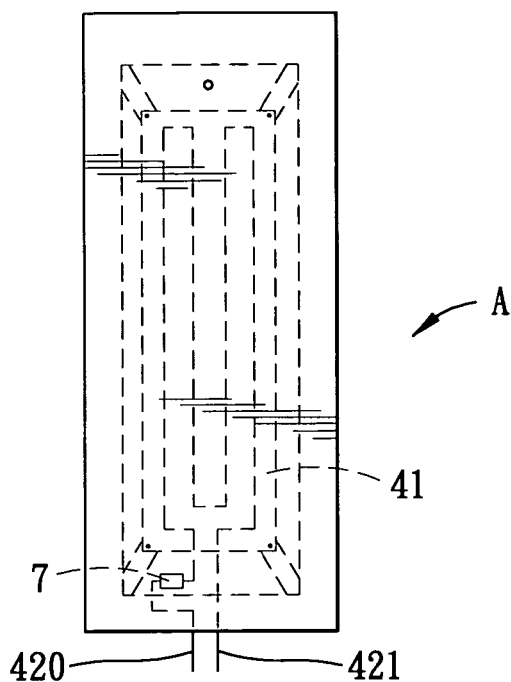
FIG. 4 is a plan view of a modified form of the heating pad of FIG. 3.

As shown in FIG. 4, a thermal control switch 7 may be provided additionally in the heating pad (A) in series connection with the heating element 41. The control switch 7 serves to control the temperature of the heating pad (A) so that, when the heating pad (A) reaches a predetermined temperature, the heating unit 4 is disconnected automatically from the power source. Generally, the temperature which is practical for a therapeutic heating pad is about 35° C. If the phase change material (also known as a thermal storage material) 5 used in the heating pad (A) is a material which is convertible from a solid state to a liquid state within a temperature range of about 29° C.–30° C. and which can be heated to a temperature up to 45° C. in its liquid state, in order to keep the temperature of the heating pad (A) within a practical range or to prevent the temperature of the heating pad (A) from rising to 45° C., the control switch 7 can act to control the electrical connection between the heating unit 4 and the power source so that the heating unit 4 is disconnected from the power source when the temperature of the phase change material 5 reaches a preset temperature. On the other hand, the control switch 7 may be arranged in such a manner that it re-connects the heating element 41 to the power source when the temperature of the heating pad (A) is lower than a preset temperature by 3° C. As such, the consumption of electrical energy can be minimized and the service life of the heating pad (A) can be prolonged.

Figure 5:
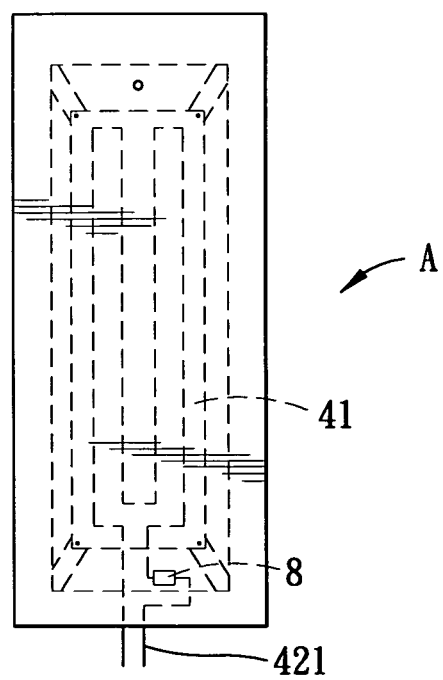
FIG. 5 is a plan view of another modified form of the heating pad of FIG. 3.

Referring to FIG. 5, the heating pad (A) may be further provided with a light emitting diode 8 adjacent to the electrodes 421 as an indicator for indicating an operative state of the heating pad (A).

Figure 6:
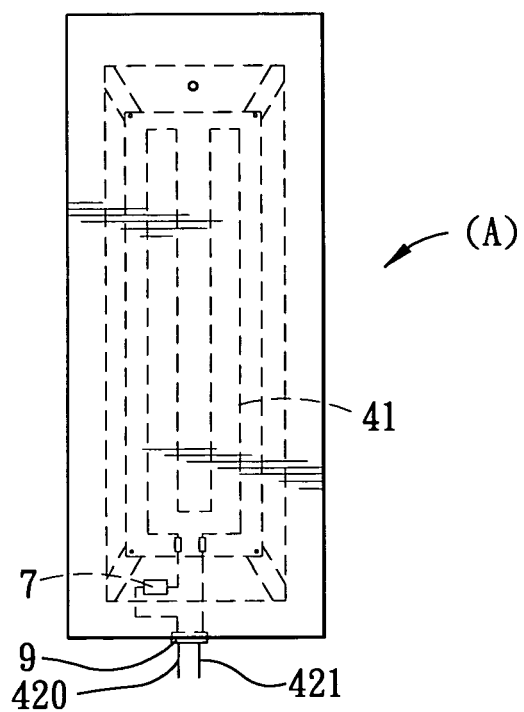
FIG. 6 is the same view as FIG. 4 but with a connector being added to the heating pad.
Figure 7:
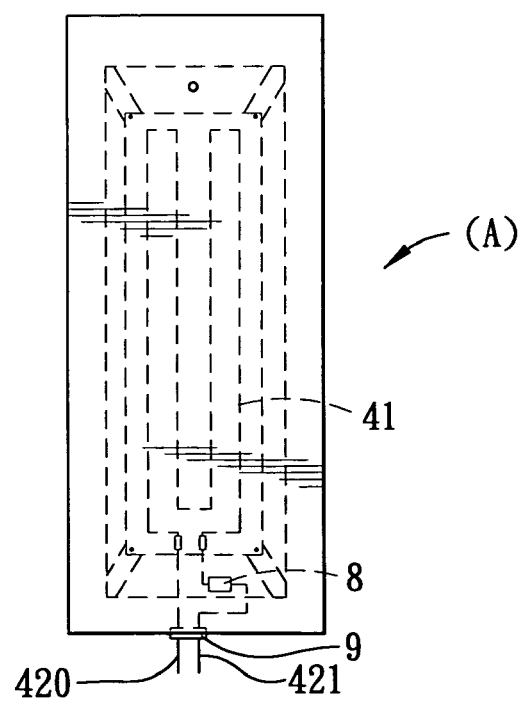
FIG. 7 is the same view as FIG. 5 but with a connector being added to the heating pad.

The arrangements shown FIGS. 4 and 5 may be modified to incorporate a connector 9 as shown in FIGS. 6 and 7. The connector 9 may be a plug connector or a socket connector, and may be connected directly to the ends of the electrodes 420, 421. Through the connector 9, the heating pad (A) can be conveniently connected to the power source.

While the present invention has been described in connection with what is considered the most practical and preferred embodiments, it is understood that this invention is not limited to the disclosed embodiments but is intended to cover various arrangements included within the spirit and scope of the broadest interpretations and equivalent arrangements.

I claim:

1. A heating pad comprising:
    an envelope confining a receiving space;
    a heating unit including a metal plate, and a resistance heating element attached to said metal plate;
    a positioning unit mounted within said receiving space and connected to said metal plate;
    a phase change material provided within said receiving space and enclosing said heating unit; and
    a pair of electrodes connected to said heating element and extending outwardly of said envelope,
    wherein said positioning unit includes a plurality of flexible strips each of which has one end attached to said envelope and another end connected to said metal plate.

2. The heating pad as claimed in claim 1, wherein said flexible strips and said envelope are made of the same material.

3. The heating pad as claimed in claim 2, wherein said metal plate is formed with holes, each of said strips passes through one of said holes.

4. The heating pad as claimed in claim 3, wherein said envelope has a plurality of corners, said strips being attached respectively to said corners.

5. The heating pad as claimed in claim 1, wherein said envelope is made of a plastic material.

6. The heating pad as claimed in claim 1, wherein said resistance heating element is a printed resistance wire provided on a surface of said metal plate.

7. The heating pad as claimed in claim 1, further comprising a thermal control switch connected electrically to said heating unit.

8. The heating pad as claimed in claim 1, further comprising a light emitting diode connected electrically to said heating unit.

9. The heating pad as claimed in claim 1, further comprising a connector connected to said electrodes externally of said envelope.

* * * * *